United States Patent
Kennedy et al.

(10) Patent No.: US 7,105,622 B2
(45) Date of Patent: Sep. 12, 2006

(54) HYBRID POLYURETHANES

(75) Inventors: Joseph P. Kennedy, Akron, OH (US); Ralf M. Peetz, Akron, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 10/858,710

(22) Filed: Jun. 2, 2004

(65) Prior Publication Data

US 2005/0272894 A1    Dec. 8, 2005

(51) Int. Cl.
*C08G 18/32* (2006.01)

(52) U.S. Cl. ............... 528/37; 528/44; 528/85; 556/460; 556/479

(58) Field of Classification Search ............ None
See application file for complete search history.

(56) References Cited

U.S. PATENT DOCUMENTS

| | | | |
|---|---|---|---|
| 3,639,354 A | 2/1972 | Leverkusen et al. | 260/77.5 AP |
| 3,957,717 A | 5/1976 | Harada et al. | 260/37 SB |
| 4,725,662 A | 2/1988 | Kuga et al. | 528/80 |
| 4,900,779 A | 2/1990 | Leibfried | 524/862 |
| 5,070,173 A | 12/1991 | Yokota et al. | 528/85 |
| 5,106,609 A | 4/1992 | Bolich, Jr. et al. | 424/70 |
| 5,534,609 A | 7/1996 | Lewis et al. | 528/15 |
| 5,968,656 A | 10/1999 | Ezenyilimba et al. | 428/423.1 |
| 6,005,051 A | 12/1999 | Kennedy et al. | 525/106 |
| 6,187,827 B1 | 2/2001 | Mukherjee et al. | 521/47.5 |
| 6,271,309 B1 | 8/2001 | Roberts et al. | 525/106 |
| 6,482,912 B1 | 11/2002 | Boudjouk et al. | 528/15 |

FOREIGN PATENT DOCUMENTS

| | | |
|---|---|---|
| EP | 0 572 183 B1 | 5/1993 |
| EP | 0 621 281 B1 | 4/1994 |
| JP | 5430300 * | 6/1979 |
| WO | WO 95/03364 | 7/1994 |
| WO | WO 99/46343 | 3/1999 |

OTHER PUBLICATIONS

"Novel Hybrid Polyurethanes" authored by Kennedy et al. and published in Polymeric Materials: Science and Engineering (2003) 89, 71-72.*

"Dendritic Carbosilanes Containing Hydroxy Groups on the Periphery" authored by Kim et al. and published in the Jounral of Organometallic Chemistry (1999) 588(1), 1-8.*

* cited by examiner

*Primary Examiner*—Marc S. Zimmer
(74) *Attorney, Agent, or Firm*—Roetzel & Andress; George W. Moxon, II

(57) ABSTRACT

Cyclosiloxane-multiol compositions, multicomponent polyurethane networks, and related methods are disclosed.

22 Claims, 1 Drawing Sheet

HYBRID POLYURETHANES

FIELD OF THE INVENTION

This invention is generally directed to multiol compositions, multicomponent networks, and related methods. More specifically, this invention is generally directed to cyclosiloxane-multiol compositions, multicomponent polyurethane networks, and related methods.

BACKGROUND OF THE INVENTION

Multicomponent networks, i.e., networks having two or more components, are known. Bicomponent and tricomponent networks are examples of such networks. And the utility of multicomponent networks is widespread and directed to applications suited to a particular network's physical characteristics. Known uses of prior-art multicomponent networks typically include amphiphilic networks used in ophthalamic applications.

Bicomponent networks (BCN's) traditionally have shown that the two crosslinked components at least contribute theoretically to the physical and chemical characteristics of the network. That is, the properties of a bicomponent network will reflect those of its individual components. For example, bicomponent networks containing polyisobutylenes and polysiloxanes may be of great interest to the extent that polyisobutylene is known for low cost, superior mechanical properties, extremely-low gas permeability, and excellent environmental, hydrolytic, and high temperature resistance while, in contrast, siloxanes are relatively expensive, have poor mechanical properties, but excel in regard to high gas permeability, low surface energy and bicompatibility. Thus, it is believed that elastomeric BCN's with varying ratios of polyisobutylene to polysiloxane such as polydimethylsiloxane may be of use to control gas permeability, water repellency, environmental stability, and biocompatibility.

It will be appreciated that BCN's may be formed from two components, but the second component may be used in such small and insignificant amounts that the second component doesn't contribute to the network's physical and chemical characteristics. In this instance, the network is not considered a "bicomponent network" as defined hereinabove, inasmuch as the properties of the network are essentially the same as the properties of the primary (first) component.

The prior art needs multicomponent networks having siloxane and polyurethane components due to the physical properties that such a network would possess.

SUMMARY OF THE INVENTION

The present invention is directed to a cyclosiloxane multiol having the formula:

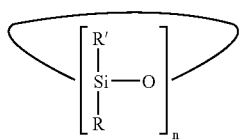

wherein R is an alcohol functional group;
wherein R' is a hydrocarbon moiety; and
wherein n is an integer greater than 1.

The present invention is further directed to a method for making a cyclosiloxane multiol comprising the step of reacting a cyclosiloxane of the formula:

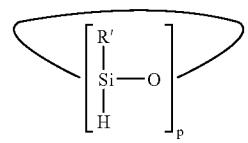

with a plurality of straight or branched allyl alcohols,
wherein R' is a hydrocarbon moiety; and
wherein p is an integer greater than 1.

The present invention is further directed to a multicomponent polyurethane network comprising the reaction product of a plurality of cyclosiloxane multiols of the formula:

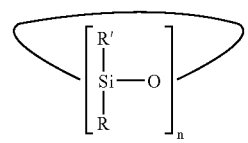

with a plurality of multi-isocyanates of the formula:

wherein R is an alcohol functional group;
wherein R' is a hydrocarbon moiety;
wherein R" is a hydrocarbon moiety;
wherein n is an integer greater than 1; and
wherein V is an integer greater than or equal to 2.

Still further, this invention is directed to a method for synthesizing a multi-component polyurethane network comprising the step of:
reacting a plurality of cyclosiloxane multiol reactants of the formula:

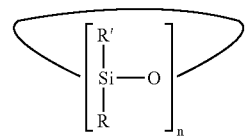

with a plurality of multi-isocyanate reactants of the formula:

wherein R is an alcohol functional group;
wherein R' is a hydrocarbon moiety;
wherein R" is a hydrocarbon moiety;
wherein n is an integer greater than 1; and
wherein V is an integer greater than or equal to 1.

Also, this invention is directed to a method that uses multicomponent polyurethane networks in biomedical applications.

A multicomponent network (MCN) is made up of two or more types of components. Nonlimiting examples of MCN's are bicomponent networks (BCN) and tricomponent networks (TCN), which have two and three types of components, respectively. Each network component is chemically bonded to at least one other network component.

A moiety is a portion of a chemical compound that is generally unreactive.

A functional group is a portion of a chemical compound that can react with another reactant.

Urethane is commonly known in the art, and the characteristic forms of urethane are:

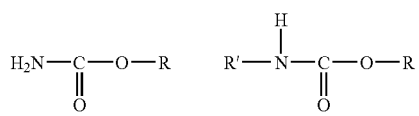

wherein both R and R' are organic moieties or organic functional groups.

As previously stated, polyurethanes are known. And they typically result from a condensation reaction of at least one polyisocyanate-containing reactant and at least one alcohol-containing reactant.

A derivative component is a part of a multicomponent polyurethane network that was derived from a particular reactant. In other words, when a plurality of cyclosiloxane multiols react with a plurality of isocyanate-containing reactants, their reaction product is a poyurethane multicomponent network. The network components that were derived from the cyclosiloxane multiol reactants are the cyclosiloxane-multiol derivative components. Likewise, the network components that were derived from the isocyanate-containing reactants are the polyurethane derivative components.

A multiol is a compound having one or more hydroxy functional groups.

The polyurethane networks can be formed into clear sheets. An advantageous physical property of the multicomponent polyurethane network is its significant $O_2$-permeability in combination with good mechanical properties, making it useful, for example, in biomedical applications.

DETAILED DESCRIPTION OF ILLUSTRATIVE EMBODIMENTS

Figure 1:
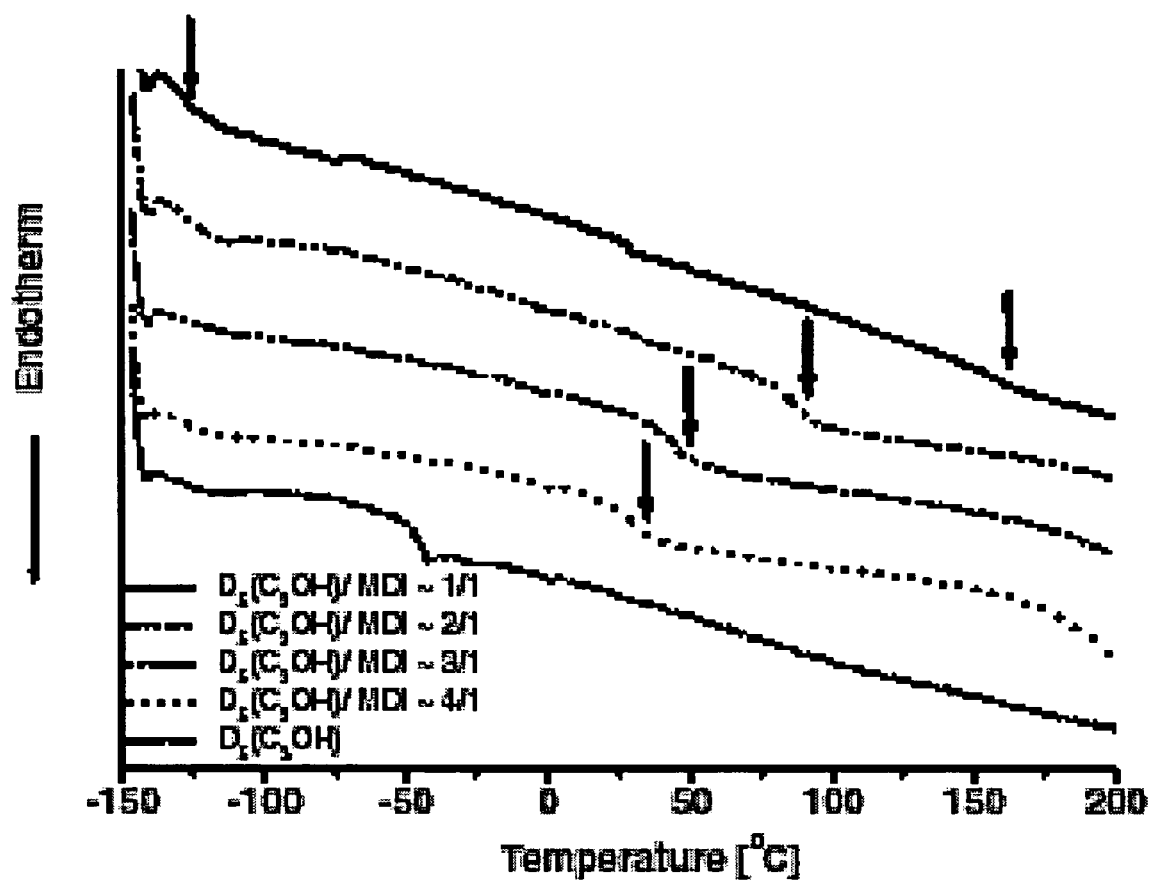
FIG. 1 is a summary of DSC traces of polyurethane-containing multicomponent networks.

This invention is generally directed to cyclosiloxane multiols, multicomponent polyurethane networks, and related methods of manufacture and use.

Cyclosiloxane multiols generally have the following chemical structure:

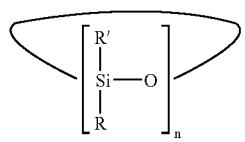

wherein R is an alcohol functional group; wherein R' is a hydrocarbon moiety; and wherein n is an integer greater than one. R can be any alcohol functional group, and nonlimiting examples include methanol, ethanol, propanol, butanol, and pentanol. The preferred alcohol functional group is propanol.

R' can be any hydrocarbon moiety and nonlimiting examples include alkyl moieties such as methyl, ethyl, propyl, and butyl. The preferred hydrocarbon moiety is methyl.

n can be any integer greater than one. Preferably, n ranges from four to six, and more preferably, n is five.

Cyclosiloxane multiols are generally synthesized by reacting a cyclosiloxane of the formula:

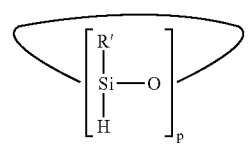

with a plurality of straight or branched allyl alcohols, wherein R' is a hydrocarbon moiety, and wherein p is an integer greater than 1.

Preferably, the variable R' is a hydrocarbon alkyl moiety. More preferably, R' is an alkyl moiety selected from the group consisting of methyl, ethyl, propyl, butyl, and pentyl. Most preferably, the hydrocarbon alkyl moiety is methyl.

The variable p indicates the number of siloxane units making up the cyclosiloxane ring. Preferably, p ranges from two to twenty, and more preferably, p ranges from four to six. Most preferably, p is five.

As previously mentioned, in synthesizing cyclosiloxane multiols, the preferred synthetic method involves reacting a cyclosiloxane with a plurality of straight or branched allyl alcohols. The preferred allyl alcohol being 2-propen-1-ol. Nonlimiting examples of additional allyl alcohols that can be employed include 2-buten-1-ol, 2-penten-1-ol, and other 2-alken-1-ols.

Synthesizing cyclosiloxane multiols can be conducted using known synthetic methods, and preferably the reaction is conducted in a liquid medium. The reaction can be performed neat or in a reaction solvent. Nonlimiting examples of employable reaction solvents include hydrocarbons, ethers, and combinations thereof. The preferred solvent being tetrahydrofuran.

In synthesizing cyclosiloxane multiols, the mole ratio of cyclosiloxane to allyl alcohol in the reaction mixture can vary depending on the number of siloxane units making up the cyclosiloxane reactants. And more specifically, the reaction mole ratio can vary depending on the number of Si—H functional groups on the cyclosiloxane ring(s). Generally, the reaction mixture provides a mole ratio of vinyl alcohol functional groups to Si—H functional groups of at least 1:1. Preferably, there are at least 1.1 vinyl alcohol functional groups for each Si—H functional group in the reaction nature. More preferably, there are at least 1.25 vinyl alcohol functional groups for each Si—H functional group in the reaction mixture. Still more preferably, there are at least 2 vinyl alcohol functional groups for each SiH functional group in the reaction mixture. Where the preferred cyclosiloxane reactant pentamethylcyclopentasiloxane ($D_5H$) is employed, there is preferably at least 1 vinyl alcohol functional group for each Si—H functional group in the reaction mixture.

The general reaction is as follows:

Nonlimiting examples of catalysts that can be used to synthesize cyclosiloxane multiols include all known hydrosylation catalytic systems. The preferred catalyst being the platinum-based Pt(dvs) ("Karstedt's catalyst").

The mole ratio of catalysts to cyclosiloxane Si—H functional groups can range from about 1:1000 to about 1:50,000. Preferably, the mole ratio of catalysts to cyclosiloxane Si—H functional groups generally ranges from about 1:10,000 to about 1:20,000. Catalytic stoichiometry can be determined by one of oridinary skill in the art without undue experimentation.

Cyclosiloxane multiol synthesis reactions are generally conducted at a temperature ranging from about 15 to about 110° C. Preferably, the temperature ranges from about 30 to about 50° C.

The cyclosiloxane multiol synthesis reactions generally go to completion in a time frame ranging from about 1 to about 3 hours. Preferably, the reactions go to completion in about 2 hours.

Reaction conditions for synthesizing a cyclosiloxane multiol can be determined by one of ordinary skill in the art without undue experimentation.

This invention's multicomponent networks have at least two components. The first component being a cyclosiloxane-multiol derivative component and the second component being a polyurethane component. The polyurethane components are derived from the isocyanate-containing reactants, and the cyclosiloxane-multiol derivative components are derived from the cyclosiloxane-multiol reactants. A nonlimiting example of this invention's polyurethane multicomponent networks is illustrated by the following drawing:

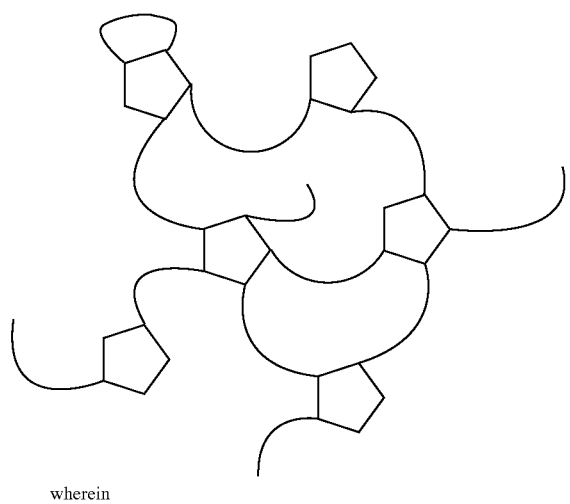

wherein

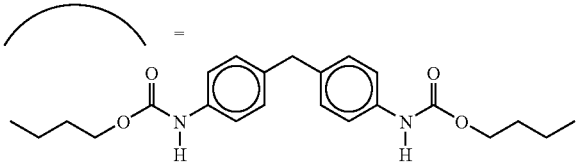

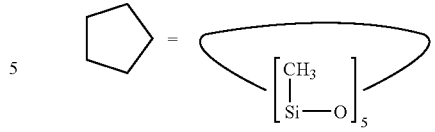

As mentioned above, the multicomponent polyurethane networks have at least two distinct components: a cyclosiloxane-multiol derivative component and a polyurethane component. In a multicomponent network, the cyclosiloxane-multiol derivative component is at least bonded to a polyurethane component or another cyclosiloxane-multiol derivative component. Preferably, the cyclosiloxane-multiol derivative component is bonded to at least two polyurethane components.

This invention is not limited by the mole ratio of cyclosiloxane-multiol derivative components to polyurethane components within a multicomponent network. But generally, the mole ratio of cyclosiloxane-multiol derivative components to polyurethane components ranges from about 1:5 to about 15:5. Preferably, the ratio of cyclosiloxane-multiol derivative components to polyurethane components ranges from about 2:5 to about 10:5. More preferably, the ratio ranges from about 2:5 to about 8:5.

It is not necessary that all of the cyclosiloxane-multiol derivative components be the same (i.e., homogeneous) within a given network. A network's cyclosiloxane-multiol derivative components can be heterogeneous. For example, a multicomponent network can have a cyclosiloxane-multiol derivative component that is a penta(hydroxypropyl)pentamethylcyclopentasiloxane-derivative component in combination with another distinct cyclosiloxane-multiol derivative component such as a hexacyclosiloxane-multiol derivative component. Preferably, the multicomponent networks have only penta(hydroxypropyl)penta-methylcyclopentasiloxane-derivative component and a polyurethane component. But various combinations of cyclosiloxane-multiol derivative components (e.g., combinations of buta, penta, hexa, and hepta cyclosiloxane-multiol derivative components) can be employed with the polyurethane components.

The cyclosiloxane-multiol derivative components preferably have at least one alkyl moiety thereon. Preferably, the number of alkyl moieties is equivalent to the number of siloxane units making up the cyclosiloxane ring. A cyclosiloxane-multiol derivative component is represented by the following drawing:

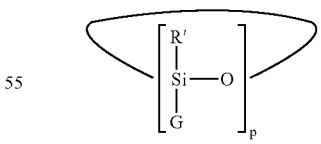

wherein the variable R' is as defined above, wherein the variable p is as defined above, and wherein the variable G is a network component.

Multicomponent polyurethane networks have at least one polyurethane component, and preferably that component is derived from a di-isocyanate reactant. The preferred di-isocyanate reactant from which the polyurethane component is prepared is 4,4'-methylenebis(phenyl isocyanate) (MDI).

And, although MDI is the preferred di-isocyanate from which the polyurethane component is prepared, other isocyanate-containing reactants can be employed. Nonlimiting examples of isocyanate-containing reactants that can be employed are toluidene diisocyanates; 1,4 diisocyanate butane; and cyclohexyl diisocyanate.

It is not necessary that all of a multicomponent network's polyurethane components be the same (i.e., homogeneous). MDI-derivative components (i.e., polyurethane components) are preferred in making up the multicomponent networks, but homogeneity of the polyurethane components is not required. That means that two or more distinct polyurethane components can be employed in a multicomponent network.

The equilibrium degree of swelling, $d_{sw}$, was determined by swelling membranes in water, hexane, or THF at room temperature until equilibrium swelling was reached. Thus, dry preweighed membrane samples were placed in a solvent-filled beaker; the samples were removed periodically from the beaker; the excess solvent on the surfaces of the samples was removed by blotting with paper; and the weights of the solvent-swollen samples were determined. The degree of swelling was calculated by:

$$d_{sw} = \frac{w_{sw} - w_{dry}}{w_{dry}} \times 100$$

wherein $w_{sw}$ and $w_{dry}$ are the weights of the swollen and dry samples, respectively.

This invention's polyurethane networks demonstrate swelling characteristics in various liquid mediums. In water, the networks generally swell from about 0.5 to about 15 percent. Preferably, they swell from 1 to 10 percent. And more preferably, they swell from about 1.1 to about 6.5 percent in water.

In hexane, this invention's polyurethane networks generally swell from about 0 to about 2 percent. More preferably, they swell from about 0 to about 1 percent.

In tetrahydrofuran (THF), this invention's polyurethane networks generally swell from about 30 to about 150 percent. Preferably, the networks swell from about 30 to about 90 percent. And more preferably, they swell from about 45 to about 85 percent in THF.

Dynamic advancing and receding contact angles ($\theta_A$ and $\theta_R$) were determined by the use of a Cahn DCA-312 microbalance by immersion and withdrawal of dried sample membranes in and out of water at ambient temperatures. The platform speed was 0.2 mm/sec. Several (5–7) cycles of immersion and withdrawal were performed until equilibrium was reached. The following equation was used to calculate the surface tension and contact angles:

$$F = \frac{\sigma P \cos(\theta)}{g}$$

wherein F is the sample force at zero immersion depth as determined by the balance (mg), P is the perimeter of the sample at the interface (cm), J is the surface tension (dyue/cm), $\theta$ is the contact angle, and g is the acceleration due to gravity (0.98 cu/sec$^2$).

The contact angles for this invention's polyurethane networks for advancing angles range from about 95 to about 120. More preferably, this invention's advancing contact angles range from about 101 to about 111.

A polyurethane network for receding angles can range from about 35 to about 60. Preferably, the receding angles range from about 39 to about 54.

Dry tensile samples were kept in a vacuum oven at temperatures between 40 and 60° C. with applied vacuum for a period of 2–4 days (until weight Constance).

Ambient tensile samples were kept openly in the laboratory under ambient conditions for a period of 2–3 weeks (until weight Constance).

Wet tensile samples were immersed in water at ambient temperatures for a period of 2–4 days (until weight Constance).

A polyurethane multicomponent network's tensile properties provide additional physical defining characteristics to the network. For instance, dry polyurethane networks typically have a break strain ranging from about 5 to about 60 MPa. Additionally, the dry networks have a modulus ranging from about 500 to about 3000 MPa, and an elongation ranging from about 2 to about 10%. More preferably, the dry networks have a break strain ranging from about 8 to about 55 MPa. Additionally, the preferred modulus ranges from about 800 to about 2200 MPa, and the elongation ranges from about 3 to about 8%.

Ambient polyurethane multicomponent networks preferably have a break strain ranging from about 10 to about 40 MPa, a modulus ranging from about 600 to about 2500 MPa, and an elongation ranging from about 2 to about 20%. More preferably, ambient networks have a break strain ranging from about 12 to about 35 MPa, a modulus ranging from about 800 to about 2000 MPa, and an elongation ranging from about 5 to about 15%.

This invention's wet polyurethane multicomponent networks have a break strain that ranges from about 5 to about 45 MPa, a modulus ranging from about 600 to about 2500 MPa, and an elongation ranging from about 10 to about 90% MPa. More preferably, this invention's wet polyurethane networks have a break strain ranging from about 8 to about 27 MPa, a mudulus ranging from about 800 to about 2000 MPa, and an elongation ranging from about 9 to about 50%.

Polyurethane multicomponent networks can be produced by reacting a plurality of isocyanate-containing reactants with a plurality of cyclosiloxane-multiol reactants. Any isocyanate-containing reactant can be employed in synthesizing polyurethane multicomponent networks. Preferably, the isocyanate-containing reactants have multiple isocyanate functional groups. For instance, di, tri, and tetra isocyanate-containing reactants can be employed in synthesizing a multicomponent network. The preferred isocyanate containing reactant is MDI, but other employable isocyanate-containing reactants include toluidene diisocyanates; 1,4 diisocyanate butane; and cyclohexyl diisocyanate.

Any cyclosiloxane multiol can be used to synthesize this invention's polyurethane networks. Cyclosiloxane multiols and their synthetic methods have been described hereinabove. Although any cyclosiloxe multiol can be employed in synthesizing this invention's polyurethane networks, there are preferred cyclosiloxane multiol reactants. Notably, penta (hydroxypropyl)pentamethylcyclopenta-siloxane [$D_5$($C_3$OH)] is the preferred cyclosiloxane multiol reactant.

More generally, the cyclosiloxane-multiol reactants used to prepare the multicomponent networks typically have alcohol functional groups that can be selected from the nonlimiting group of methanol, propanol, butanol, and pentaol. Further, there is no limitation on the alcohol functional groups that can be employed in synthesizing a multicomponent network. The preferred alcohol functional group is propanol.

Homogeneous alcohol functional groups on a cyclosiloxane multiol are not required in order to perform the reaction. That is to say that the alcohol functional groups within a particular cyclosiloxane reactant can vary. For example, a cyclosiloxane multiol reactant can have at least two distinct alcohol functional groups within the compound—such as propanol and ethanol functional groups.

In addition to the alcohol functional groups on the cyclosiloxane multiol reactants, there are alkyl moieties on the cyclosiloxane-multiol reactants. Preferably, the number of alkyl moieties directly correlates to the number of siloxane units within the cyclosiloxane ring. For example, a pentacyclosiloxane multiol preferably has five alkyl moieties.

Nonlimiting examples of preferred alkyl moieties include methyl, ethyl, and propyl. It is not necessary that the alkyl moieties be homogeneous throughout an entire cyclosiloxane multiol reactant. In other words, a single cyclosiloxane multiol reactant can have two or more distinct alkyl moieties such as methyl and ethyl.

In preparing the polyurethane multicomponent networks, a plurality of cyclosiloxane multiol reactants are reacted with a plurality of isocyanate reactants. In doing so, the ratio of hydroxy functional groups to isocyanate functional groups generally ranges from about 8:1 to about 1:1. Preferably, the ratio of hydroxy functional groups to isocyanate functional groups ranges from about 6:1 to about 1:1. More preferably, the ratio ranges from about 5:1 to about 1:1.

In synthesizing this invention's polyurethane networks, reaction between cyclosiloxane multiols and isocyanate reactants can generally take place at a temperature ranging from about 20 to about 150° C. Preferably, the temperature for reaction is from about 25 to about 110° C. More preferably, the polyurethane networks synthetic reaction takes place at about 50 to about 100° C.

The synthetic reaction is not limited to occurring within any specified time frame. Generally, the reaction is carried out for about 18 hours. More preferably, the reaction is carried out for about 16 hours. Most preferably, the reaction is carried out for about 12 hours.

EXPERIMENTAL

Reagents. $D_5H$ (95%) and platinumdivinyltetramethyldisiloxane complex (Pt(dvs), 2.1–2.4% Pt concentration in xylene), both from Gelest, allyl alcohol and MDI (both 99%, Aldrich) were used as received. Toluene and THF (both Fisher) were distilled from $CaH_2$ prior to use.

Characterization Methods. Details of the methodology, i.e., $^1$H-NMR-spectroscopy (300 MHz, solutions in $CDCl_3$), DSC measurements GPC(RI detector, PIB standards), $O_2$-permeability determination, tensile strength testing (ASTM Standard 638-5), and dynamic contact angle are well known as described in Journal of Polymer Science, Part A=Polymer Chemistry 2002, 40, 1285, which is incorporated by reference. DSC measurements were performed between −145° C. and 200° C. ATR/FTIR-spectroscopy was carried out with a FTIR-8300 (Shimadzu Instruments) equipped with an ATR module (MIRacle, PIKE Technologies; single reflection, diamond crystal).

Synthesis of $D_5(C_3OH)$. In a round bottom flask equipped with a reflux condenser were mixed 25 mL (83.2 mmol) $D_5H$, 35 mL (515 mmol) allyl alcohol; and 200 mL toluene. Oxygen was removed from the solution by repeatedly applying vacuum and venting with nitrogen. The flask was placed in a water bath at room temperature, and 0.24 mL of catalyst solution (100 mmolar Pt(dvs) in xylenes) was added to the mixture. After ~45 min 33 mg (0.126 mmol) $PPh_3$ were added and the solution was stirred another 60 min. The product was isolated and placed in vacuo at 50° C. for ca. 5 h. Yield 44.5 g (90%). The product, a viscous liquid, was analyzed by $^1$H-NMR-spectroscopy and GPC, and consisted of ~85% $D_5(C_3OH)$ and ~15% condensed dimer, plus traces of higher condensates.

Network Synthesis. In a vial were added 3 mL of a $D_5(C_3OH)$ solution in THF (330 mM), 604 mg (2.4 mmol) MDI, and additional 3 mL THF. The clear solution was poured into a ca. 2.5"×2.5" Teflon mold, and placed in an oven at ~30° C. After 45 min., the mold was transferred to another oven and heated at ~100° C. for 14 h. A clear sheet was obtained. All networks, except for the OH/NCO+4/1 networks, were extracted with THF, an excellent solvent for both components (4/1 networks lost their integrity upon THF extraction).

Results and Discussion. The microstructure of $D_5(C_3OH)$ was established by $^1$H NMR spectroscopy (300 MHz, $CDCl_3$) and GPC(RI detector, THF). Regarding the synthesized networks, ATR/FTIR-analysis showed no residual isocyanate functional groups, —NCO, in the 2/1, 3/1, and 4/1 OH/NCO networks. The urethane linkages could be easily identified and the spectra changed systematically as a function of network composition.

Table 1 summarizes select properties of four distinct PU networks. The degree of swelling ($d_{sw}$, %) in $H_2O$, n-$C_6H_{14}$, and THF follows the extent of the crosslinking ("tightness") as the function of relative composition: [OH]/[NCO] ~1, 2, 3, 4. Samples stored under ambient conditions (laboratory atmosphere) absorbed 0.3–0.4% $H_2O$. Surprisingly, equilibrium water uptake (samples submerged in $H_2O$) was very low (~6.5%) even for the loosest network (OH/NCO=4:1).

TABLE 1

| $D_5(C_3OH)$/MDI | | | Swelling $d_{SW}$## | | | Contact Angles | | | Tensile Properties## | | | |
| --- | --- | --- | --- | --- | --- | --- | --- | --- | --- | --- | --- | --- |
| | | | % | | | (Water)# | | | Break- | | Yield- | Elon- |
| [OH]/[NCO] | Weight % | Moles | $H_2O$ | Hexane | THF | $θ_A/θ_R$ | $θ_A - θ_R$ | Sample Condition | Strain MPa | Modulus MPa | Strain MPa | gation % |
| ~1/1 | 50/50 | 2/5 | 1.1 | 0 | 45.1 | 110/54 | 56 | Dry | 48 | 2240 | | 4 |
| | | | | | | | | Ambient | 35 | 1790 | 37 | 13 |
| | | | | | | | | Wet | 37 | 2030 | | 9 |

TABLE 1-continued

| D5(C3OH)/MDI | | | Swelling d_SW## | | | Contact Angles | | | Tensile Properties## | | | |
| --- | --- | --- | --- | --- | --- | --- | --- | --- | --- | --- | --- | --- |
| [OH]/ | | | % | | | (Water)# | | | Break-Strain | Modulus | Yield-Strain | Elongation |
| [NCO] | Weight % | Moles | H2O | Hexane | THF | $\theta_A/\theta_R$ | $\theta_A - \theta_R$ | Sample Condition | MPa | MPa | MPa | % |
| ~2/1 | 66/33 | 4/5 | 2.0 | 0.6 | 69.4 | 111/44 | 57 | Dry | | n.d. | | |
| | | | | | | | | Ambient | 36 | 2170 | | 5 |
| | | | | | | | | Wet | | n.d. | | |
| ~3/1 | 75/25 | 6/5 | 2.6 | 1.1 | 88.6 | 105/39 | 66 | Dry | | n.d. | | |
| | | | | | | | | Ambient | 24 | 1110 | 29 | 14 |
| | | | | | | | | Wet | | n.d. | | |
| ~4/1 | 80/20 | 8/5 | 6.5 | 0.9 | n.d. | 101/54 | 46 | Dry | 14 | 810 | 17 | 8 |
| | | | | | | | | Ambient | 12 | 850 | 14 | 8 |
| | | | | | | | | Wet | 8 | | | 33 |

Averages of second and third cycles
Averages of at least two determinations

The mechanical properties reflect relative compositions, i.e., the strongest networks were obtained with D5(C3OH)/MDI=1, and tensile properties declined by increasing the D5(C3OH)/MDI ratio.

The surfaces of the PUs prepared were investigated by dynamic contact angle measurements in water. The advancing angle, $\theta_A \sim 110°$, corresponds well to literature values for PDMS, indicating the presence of cyclosiloxane units at the surface. However, the receding angles $\theta_R$ are ~60° smaller. This large hysteresis is most likely due to a reorganization that brings the polar structural units near the surface in water.

FIG. 1 shows a summary of DSC traces of the PUs prepared, together with that of D5(C3OH). Each thermogram shows at least two Tg's. The thermogram of D5(C3OH) exhibits a weak and a strong transition at ~−122° and ~−44° C., respectively. These thermal transitions are in line with the transition of D5H. The transition at ~−122° C. is readily identifiable in the various PUs, and its position remains unchanged. In contrast, the transition at ~−44° C. shifts to higher temperatures, i.e., to ~38, 47, 82, and 149° C., with D5(C3OH)/MDI=4, 3, 2, and 1. Evidently, the cyclosiloxane units exhibit a Tg at ~−122° C., while the structurally more rigid "bridges" between the rings are responsible for the higher Tg's. The shifting of the Tg in these cases may be a function of the varying "tightness" of the networks.

Investigations regarding O2-permeability have been performed. For the 1/1 networks the permeability was ~115 barrer. The findings also suggest substantially higher values for the networks with D5(C3OH)/MDI>1.

What is claimed is:

1. A cyclosiloxane multiol having the formula:

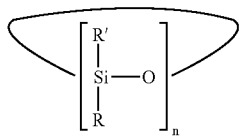

wherein R is an alcohol group containing at least 31 carbon atoms;
wherein R' is a hydrocarbon moiety; and
wherein n is an integer equal to 4, 5, or 6.

2. The multiol of claim 1, wherein R is a propanol group.

3. The multiol of claim 1, wherein R' is a methyl moiety.

4. A cyclosiloxane multiol having the formula:

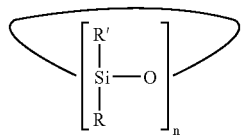

wherein R is an alcohol group;
wherein R' is a hydrocarbon moiety; and
wherein n is 5.

5. The multiol of claim 1, wherein each R and R' is independently selected for each cyclosiloxane multiol unit.

6. A method for making a cyclosiloxane multiol comprising the step of:

reacting a cyclosiloxane of the formula:

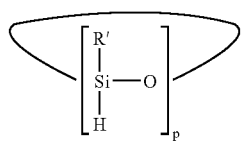

with a plurality of strait straight or branched allyl unsaturated alcohols,
wherein R' is a hydrocarbon moiety, and
wherein p is an integer equal to 4, 5, or 6.

7. The method of claim 6 wherein each R' is independently selected for each cyclosiloxane unit.

8. The method of claim 6 wherein R' is methyl, ethyl, propyl, butyl, or pentyl.

9. The method of claim 6 wherein R' is methyl.

10. A multicomponent network comprising the reaction product of a plurality of cyclosiloxane multiols of the formula:

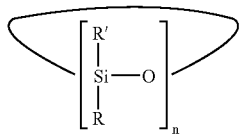

with a plurality of multi-isocyanates of the formula:

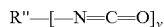

wherein R is an alcohol group;
wherein R' is a hydrocarbon moiety;
wherein R" is a hydrocarbon moiety;
wherein n is an integer greater than one; and
wherein V is an integer greater than or equal to one.

11. The network of claim 10, wherein R is a propanol group.

12. The network of claim 10, wherein R' is a methyl moiety.

13. The network of claim 10, wherein n is 4, 5, or 6.

14. The network of claim 10, wherein n is 5.

15. The network of claim 10, wherein each R and R' is independently selected for each multiol unit.

16. The network of claim 10, wherein V is two.

17. The network of claim 10, wherein the plurality of isocyanates are 4,4'-methylenebis(phenyl isocyanate).

18. The multicomponent network of claim 10, wherein each cyclosiloxane multiol is independently selected.

19. The multicomponent network of claim 10, wherein each multi-isocyanate is independently selected.

20. The multicomponent network of claim 10, wherein R is a propanol group;
wherein R' is a methyl moiety;
wherein n is an integer equal to 4, 5, or 6; and
wherein V is two.

21. The multicomponent network of claim 10, wherein the plurality of cyclosiloxane multiol reactants are penta(hydroxypropyl)-pentamethylcyclopentasiloxane reactants, and wherein the plurality of multi-isocyanate reactants are 4,4'-methylenebis (phenyl isocyanate).

22. A method for synthesizing a polyurethane network comprising the step of:
reacting a plurality of cyclosiloxane multiol reactants of the formula:

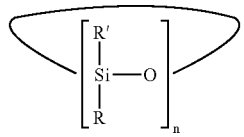

wherein R is an alcohol group;
wherein R' is a hydrocarbon moiety; and
wherein n is an integer greater than one,
with a plurality of multi-isocyanate reactants of the formula:

wherein R" is a hydrocarbon moiety; and
wherein V is an integer greater than or equal to one.

* * * * *